United States Patent [19]

Meilland

[11] Patent Number: Plant 5,607

[45] Date of Patent: Dec. 24, 1985

[54] ROSE PLANT-MEIKOLA VARIETY

[75] Inventor: Marie L. Meilland, Antibes, France

[73] Assignee: The Conard-Pyle Company, West Grove, Pa.

[21] Appl. No.: 571,203

[22] Filed: Jan. 16, 1984

[51] Int. Cl.[4] ..... A01H 5/00

[52] U.S. Cl. ..... Plt./18

[58] Field of Search ..... Plt./18

*Primary Examiner*—Robert E. Bagwill

*Attorney, Agent, or Firm*—Burns, Doane, Swecker & Mathis

[57] ABSTRACT

A new and distinct variety of Hybrid Tea rose plant is provided having large attractive double blossoms which are light Venetian pink in coloration. The edges of the outer surfaces of the petals are lightly shaded with fuchsine. The new variety is well adapted for the production of cut flowers while being grown under greenhouse cultivation.

16 Drawing Figures

SUMMARY OF THE INVENTION

The new and distinct variety of Hybrid Tea rose plant of the present invention was created by artificial pollination wherein two parents were crossed which previously had been studied for the characteristics sought. Both the seed parent and the pollen parent were unnamed seedlings. The parentage of the pollen parent of the new variety can be summarized as follows:

[[MEIALFI×(MEGER×MEGAN)]×GOLDEN GARNETTE]×unnamed seedling.

The variety GOLDEN GARNETTE from which the pollen parent was partially derived is the subject of U.S. Plant Pat. No. 1,898.

The seeds resulting from the above pollination were sown and 85 plantlets were obtained which were physically and biologically different from each other. Selective study resulted in the identification of a single plant of the new variety. The desirable qualities of the new variety have been confirmed through extensive testing and the importance of the new variety has been firmly established.

It was found that the new variety of Hybrid Tea Rose plant of the present invention possesses the following characteristics:

(a) from the physical point of view, the plant has medium green adult wood, an erect growth habit, and forms large attractive double blossoms which are Venetian pink on the inner and outer surfaces with the outer surfaces of the petals being lightly shaded with fuchsine on the edges, and (b) from the biological point of view, the plant has vigorous vegetation, and produces an abundance of long lasting blossoms.

The blossoms of the new variety are of long duration and the petals detach well.

The new variety has been found to undergo propagation by budding, grafting, and cuttings. The characteristics of the new variety have been found to be strictly transmissible by such asexual propagation.

The rose plant of the new variety has been designated the MEIKOLA variety.

BRIEF DESCRIPTION OF THE PHOTOGRAPH

The accompanying photograph shows as nearly true as it is reasonably possible to make the same in a color illustration of this character, typical specimens from one year old plants of plant parts of the new variety when observed during June. The rose plants of the new variety described herein were grown at Cannet des Maures, Var, France, in a greenhouse and were grafted on *Rosa indica* rootstock.

DETAILED DESCRIPTION

Figures 1, 2, 3, 4, 5, 6, 7, 8, 9, 10, 11, 12, 13, 14, 15, 16:
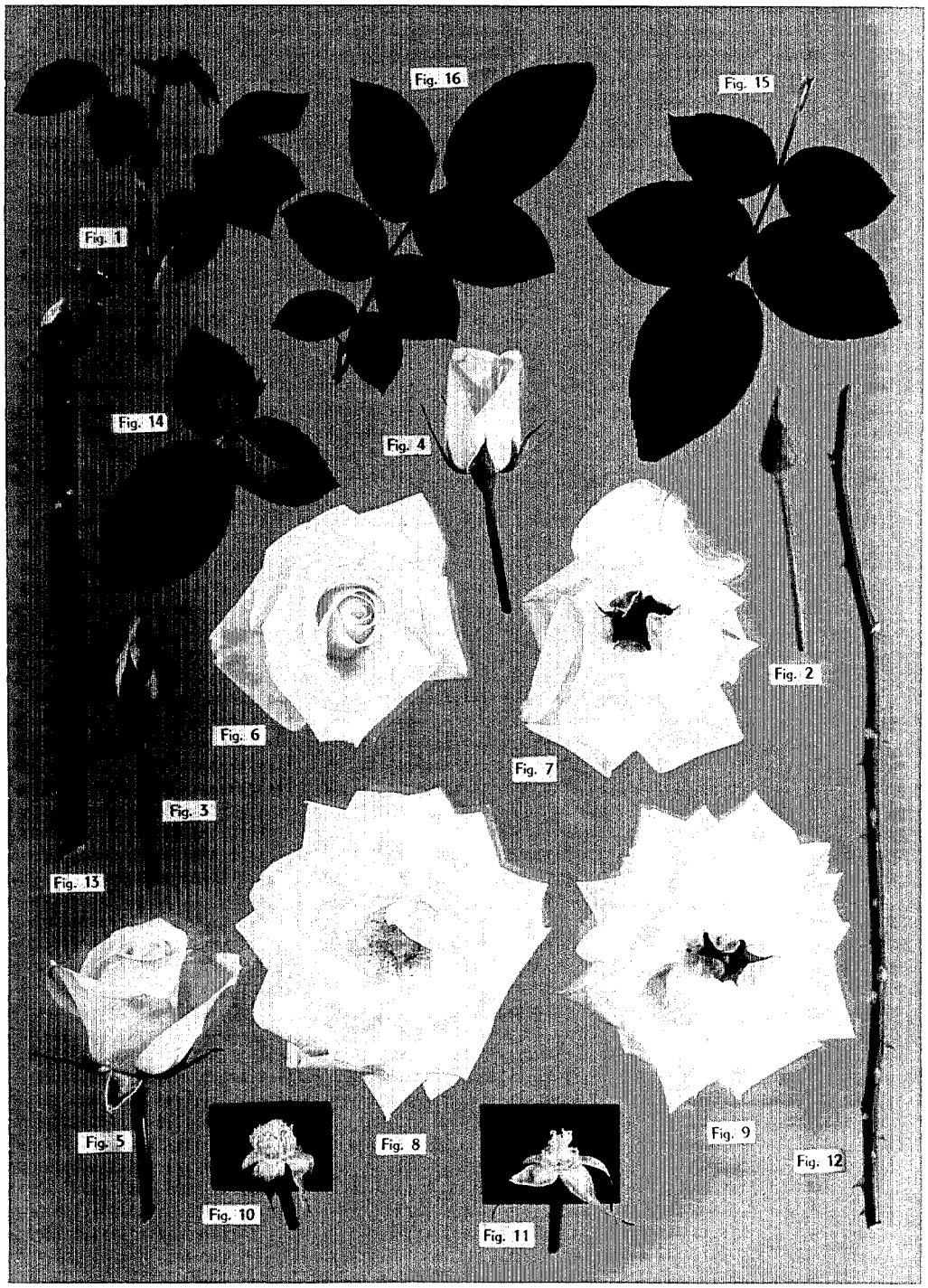
FIG. 1 illustrates a specimen of a young shoot.
FIG. 2 illustrates a specimen of a bud before the opening of the sepals.
FIG. 3 illustrates a specimen of a bud as the sepals begin to open.
FIG. 4 illustrates a specimen of a bud as the petals begin to open.
FIG. 5 illustrates a specimen of a flower at the beginning of opening.
FIG. 6 illustrates a specimen of a flower in the course of opening—plan view-obverse.
FIG. 7 illustrates a specimen of a flower in the course of opening—plan view-reverse.
FIG. 8 illustrates a specimen of a fully open flower—plan view-obverse.
FIG. 9 illustrates a specimen of a fully open flower—plan view-reverse.
FIG. 10 illustrates a specimen of a floral receptacle showing the arrangement of the stamens (sepals being removed)
FIG. 11 illustrates a specimen of a floral receptacle showing the arrangement of the pistils (petals and stamens being removed)
FIG. 12 illustrates a specimen of a young flowering stem.
FIG. 13 illustrates a specimen of mature wood.
FIG. 14 illustrates a specimen of a leaf with three leaflets—under surface.
FIG. 15 illustrates a specimen of a leaf with five leaflets—upper surface.
FIG. 16 illustrates a specimen of a leaf with seven leaflets—upper surface.

The chart used in the identification of the colors is that of The Royal Horticultural Society (R.H.S. Colour Chart). The terminology preceding the numbered references has been added to designate in common terms, the corresponding colors.

Class: Hybrid Tea.

Plant:

*Height.*—When plants are pruned to 85 cm., flower-bearing stems of approximately 70 to 80 cm. in length are produced. Accordingly, the plant commonly has a height of 1.55 to 1.65 meters.

*Habit.*—Erect.

Branches:

*Color.*—Young stems: Bronzed green, Yellow-Green Group 146A. Mature wood: Medium green, Yellow-Green Group 147B.

*Thorns.*—Shape: Upper edge: Very slightly convex, slender, inflexed towards the base. Lower edge: Concave to very concave. Size: Medium. Quantity: Sparse to moderately numerous and mingled with small acicula. Color: On young stems: Greenish (was reddish In January, 1983). On mature wood: Straw colored, then Havana brown.

Leaves:

*Stipules.*—Adnate, pectinate, fairly wide and linear.

*Petioles.*—Inner surface: Grooved reddish-brown on young foliage and medium green on adult foliage with more or less glandular edges. Outer surface: Light green; a few small hooked thorns are commonly present.

*leaflets.*—Number: 1, 3, 5, and 7 most often. Shape: Generally oval with a slender base. Serration: Simple and regular. Texture: Leathery. General effect: Fairly ample foliage, dense, and has a dull cast. Color: Young foliage: Upper surface: Medium green, darker than Yellow-Green Group 147B (was flushed with reddish edges in January, 1983). Under surface: Medium green, Yellow-Green Group 148B. Color: mature foliage: Upper surface: Dark green, Yellow-Green Group 147A. Under surface: Medium green, Yellow-Green Group 148B.

Inflorescence:

*Number of flowers.*—Commonly one per stem, but sometimes the first four stipular eyes may develop.

*Peduncle.*—Straight, rigid, and smooth, its length is approximately 8 cm. on the average.

*Sepals.*—Upper surface: Tomentose, greenish in coloration. Under surface: Light green, more or less glandular; outer sepals have their edges very slightly appendiculated.

*Bud.*—Shape: Ovoid before the sepals open. Length: Fairly short, approximately 2.5 cm. on average (not including the calyx) at the opening of the sepals. Size: Medium. Color: When opening: Upper surface: Azalea pink, Red Group 38A, lightly shaded on edges of outer petals with Dawn pink, Red Group 49A. Under surface: Azalea pink, Red Group 38A, more or less shaded with fuchsine on edges.

*Flower.*—Form: Fully double, initially the sides are substantially parallel and subsequently a cup-like configuration is assumed, petals are firm and bear a small unguis on both surfaces. Diameter: Approximately 11 cm. on average. Color: When opening begins: Upper surface: Medium Venetian pink, Red Group 49B. Under surface: Medium Venetian pink, Red Group 49B, more or less shaded with fuchsine on the edges. Color: When partially open: Upper surface: Light Venetian pink, Red Group 49C. Under surface: Light Venetian pink, Red Group 49C, very slightly shaded fuchsine on the edges. Color: When fully open: Upper surface: French pink, Red Group 49D. Under surface: French pink, Red Group 49D, very slightly shaded fuchsine on the edges. Fragrance: None. Lasting quality: Medium. Corolla: Petals: Texture: Firm. Form: Rounded, the top is sometimes slightly "V" shaped. Number: Approximately 25 on average. Petal drop: Petals detach cleanly. Stamens: Number: 135 on average. Anthers: Ochre colored and slightly tinted with fuchsine in the center; situated beneath the level of the stigmas. Filaments: Yellowish in coloration, somewhat tinted with fuchsine, irregular in height. Pistils: Number: Approximately 105 on average. Stigmas: Straw colored. Styles: Straw colored with fuchsine tip, tomentose at the base. Receptacle: Light green and smooth, at the dehiscence of the anthers in longitudinal cross-section it is fairly narrow and funnel shaped.

Development:

*Vegetation.*—Vigorous.

*Blossoming.*—Abundant.

*Forcing aptitude.*—Good.

*Disease resistance.*—Very good.

I claim:

1. A new and distinct variety of Hybrid Tea rose plant characterized by the fact that from the physical point of view, the plant has medium green adult wood, an erect growth habit, and forms large attractive double blossoms which are light Venetian pink on the inner and outer surfaces with the outer surfaces of the petals being lightly shaded with fuchsine on the edges, and from the biological point of view, the plant has vigorous vegetation, and produces an abundance of long lasting blossoms, substantially as shown and described.

* * * * *